(12) United States Patent
Imran

(10) Patent No.: US 7,643,887 B2
(45) Date of Patent: Jan. 5, 2010

(54) ABDOMINALLY IMPLANTED STIMULATOR AND METHOD

(75) Inventor: Mir A. Imran, Los Altos Hills, CA (US)

(73) Assignee: IntraPace, Inc., Mountain View, CA (US)

( * ) Notice: Subject to any disclaimer, the term of this patent is extended or adjusted under 35 U.S.C. 154(b) by 612 days.

(21) Appl. No.: 11/249,291

(22) Filed: Oct. 12, 2005

(65) Prior Publication Data

US 2006/0089699 A1   Apr. 27, 2006

Related U.S. Application Data

(60) Continuation-in-part of application No. 10/295,128, filed on Nov. 14, 2002, now Pat. No. 7,509,174, which is a division of application No. 09/847,884, filed on May 1, 2001, now Pat. No. 6,535,764.

(51) Int. Cl.
*A61N 1/372* (2006.01)
(52) U.S. Cl. .......................... 607/133; 607/40
(58) Field of Classification Search ............. 607/40, 607/133
See application file for complete search history.

(56) References Cited

U.S. PATENT DOCUMENTS

| | | | |
|---|---|---|---|
| 3,411,507 A | 11/1968 | Wingrove | 128/422 |
| 3,646,940 A | 3/1972 | Timm et al. | 128/421 |
| 3,662,758 A | 5/1972 | Glover | 128/419 |
| 3,677,251 A | 7/1972 | Bowers | 128/419 |
| 3,735,766 A | 5/1973 | Bowers et al. | 128/419 |
| 3,796,221 A | 3/1974 | Hagfors | 128/421 |
| 3,815,611 A | 6/1974 | Denniston, III | 128/419 |
| 3,835,865 A | 9/1974 | Bowers | 128/419 |
| 4,102,344 A | 7/1978 | Conway | 128/419 |
| 4,135,518 A | 1/1979 | Dutcher | |
| 4,153,059 A | 5/1979 | Fravel et al. | |
| RE30,366 E | 8/1980 | Rasor et al. | 128/419 |
| 4,338,945 A | 7/1982 | Kosugi et al. | |
| 4,431,000 A | 2/1984 | Butler et al. | |

(Continued)

FOREIGN PATENT DOCUMENTS

EP    0 129 483    2/1984

(Continued)

OTHER PUBLICATIONS

C. Paul Swain, et al., An Endoscopically Deliverable Tissue-Transfixing Device For Securing Biosensors In The Gastrointestinal Tract, *Gastrointestinal Endoscopy*, 40/6:730-734 (1994).

(Continued)

*Primary Examiner*—George R Evanisko
*Assistant Examiner*—Michael Kahelin
(74) *Attorney, Agent, or Firm*—Townsend and Townsend and Crew LLP

(57) ABSTRACT

An retaining device for attaching to a contractile organ such as a digestive tract organ or stomach is provided. One aspect may include a lead for stimulating a digestive organ. The device may be an electrical stimulation device configured to deliver electrical signals to the organ. The device may be implanted in the abdomen using a laparoscopic or other method.

14 Claims, 4 Drawing Sheets

U.S. PATENT DOCUMENTS

| | | | |
|---|---|---|---|
| 4,571,556 A | 2/1986 | Gnerlich et al. | |
| 4,628,928 A | 12/1986 | Lowell | 128/303 |
| 4,690,145 A | 9/1987 | King-Smith et al. | |
| 4,699,143 A | 10/1987 | Dufresne et al. | |
| 4,823,808 A | 4/1989 | Clegg | 128/773 |
| 4,921,481 A | 5/1990 | Danis et al. | 604/67 |
| 4,925,446 A | 5/1990 | Garay | 604/96 |
| 5,111,816 A | 5/1992 | Pless et al. | |
| 5,188,104 A | 2/1993 | Wernicke et al. | 128/419 |
| 5,197,491 A | 3/1993 | Anderson et al. | 128/786 |
| 5,217,449 A | 6/1993 | Yuda et al. | 604/890 |
| 5,259,399 A | 11/1993 | Brown | |
| 5,285,781 A | 2/1994 | Brodard | |
| 5,292,344 A | 3/1994 | Douglas | 607/40 |
| 5,411,527 A | 5/1995 | Alt | |
| 5,415,181 A | 5/1995 | Hogrefe et al. | 128/736 |
| 5,423,872 A | 6/1995 | Cigaina | 607/40 |
| 5,540,730 A | 7/1996 | Terry et al. | 607/40 |
| 5,558,640 A | 9/1996 | Pfeiler et al. | 604/67 |
| 5,681,260 A | 10/1997 | Ueda et al. | |
| 5,690,691 A | 11/1997 | Chen et al. | 607/40 |
| 5,716,392 A | 2/1998 | Bourgeois et al. | 607/132 |
| 5,792,048 A | 8/1998 | Schaefer | 600/302 |
| 5,800,445 A | 9/1998 | Ratcliff | 606/116 |
| 5,836,994 A | 11/1998 | Bourgeois | 607/40 |
| 5,861,014 A | 1/1999 | Familoni | 607/40 |
| 5,902,331 A * | 5/1999 | Bonner et al. | 607/122 |
| 5,928,195 A | 7/1999 | Malamud et al. | 604/141 |
| 5,993,473 A | 11/1999 | Chan et al. | 606/192 |
| 5,995,872 A | 11/1999 | Bourgeois | 607/40 |
| 6,004,319 A | 12/1999 | Goble et al. | |
| 6,026,326 A | 2/2000 | Bardy | 607/40 |
| 6,041,258 A | 3/2000 | Cigaina et al. | 607/40 |
| 6,083,249 A | 7/2000 | Familoni | 607/40 |
| 6,091,992 A | 7/2000 | Bourgeois | 607/40 |
| 6,097,984 A | 8/2000 | Douglas | 607/40 |
| 6,098,629 A | 8/2000 | Johnson et al. | 128/897 |
| 6,104,955 A | 8/2000 | Bourgeois | 607/40 |
| 6,112,123 A * | 8/2000 | Kelleher et al. | 607/98 |
| 6,115,635 A | 9/2000 | Bourgeois | 607/40 |
| 6,205,359 B1 | 3/2001 | Boveja | 607/45 |
| 6,216,039 B1 | 4/2001 | Bourgeois | 607/40 |
| 6,243,607 B1 | 6/2001 | Mintchev et al. | 607/40 |
| 6,285,897 B1 * | 9/2001 | Kilcoyne et al. | 600/350 |
| 6,321,124 B1 | 11/2001 | Cigaina | 607/133 |
| 6,327,503 B1 | 12/2001 | Familoni | 607/40 |
| 6,366,814 B1 | 4/2002 | Boveja et al. | 607/45 |
| 6,381,495 B1 | 4/2002 | Jenkins | 607/40 |
| 6,427,089 B1 | 7/2002 | Knowlton | |
| 6,449,511 B1 | 9/2002 | Mintchev et al. | 607/40 |
| 6,453,199 B1 | 9/2002 | Kobozev | 607/40 |
| 6,454,785 B2 | 9/2002 | DeHoyos Garza | |
| 6,477,423 B1 | 11/2002 | Jenkins | 607/40 |
| 6,510,332 B1 | 1/2003 | Greenstein | 600/377 |
| 6,529,778 B2 | 3/2003 | Prutchi | 607/119 |
| 6,535,764 B2 | 3/2003 | Imran et al. | |
| 6,540,789 B1 | 4/2003 | Silverman et al. | 623/23.65 |
| 6,542,776 B1 | 4/2003 | Gordon et al. | 607/40 |
| 6,564,101 B1 | 5/2003 | Zikria | 607/40 |
| 6,571,127 B1 | 5/2003 | Ben-Haim et al. | 607/40 |
| 6,591,137 B1 | 7/2003 | Fischeli et al. | 607/40 |
| 6,600,953 B2 | 7/2003 | Flesler et al. | 607/40 |
| 6,606,518 B1 | 8/2003 | Cigaina | 607/41 |
| 6,606,523 B1 | 8/2003 | Jenkins | 607/133 |
| 6,609,025 B2 | 8/2003 | Barrett et al. | 607/2 |
| 6,611,715 B1 | 8/2003 | Boveja | 607/40 |
| 6,615,084 B1 | 9/2003 | Cigaina | 607/40 |
| 6,684,104 B2 | 1/2004 | Gordon et al. | 607/40 |
| 6,826,428 B1 | 11/2004 | Chen et al. | 607/40 |
| 6,879,859 B1 | 4/2005 | Boveja | 607/45 |
| 6,895,278 B1 | 5/2005 | Gordon | 607/40 |
| 6,895,279 B2 | 5/2005 | Loeb et al. | 607/40 |
| 6,999,819 B2 | 2/2006 | Swoyer et al. | |
| 7,020,526 B1 | 3/2006 | Zhao | |
| 7,054,692 B1 | 5/2006 | Whitehurst et al. | |
| 2002/0072780 A1 | 6/2002 | Foley | 607/40 |
| 2002/0103424 A1 | 8/2002 | Swoyer et al. | 600/350 |
| 2002/0103521 A1 | 8/2002 | Swoyer et al. | 607/116 |
| 2002/0103522 A1 | 8/2002 | Swoyer et al. | 607/116 |
| 2002/0161414 A1 | 10/2002 | Flesler et al. | 607/40 |
| 2002/0198570 A1 | 12/2002 | Puskas | 607/2 |
| 2002/0198571 A1 | 12/2002 | Puskas | 604/2 |
| 2003/0055463 A1 | 3/2003 | Gordon et al. | 607/40 |
| 2003/0055467 A1 | 3/2003 | Ben-Haim et al. | |
| 2003/0120328 A1 | 6/2003 | Jenkins | 607/2 |
| 2003/0144708 A1 | 7/2003 | Starkebaum | 607/116 |
| 2003/0195600 A1 | 10/2003 | Tronnes | 607/133 |
| 2003/0212439 A1 | 11/2003 | Schuler | 607/40 |
| 2004/0015201 A1 | 1/2004 | Greenstein | 607/40 |
| 2004/0059393 A1 | 3/2004 | Policker et al. | 607/40 |
| 2004/0088022 A1 | 5/2004 | Chen | 607/40 |
| 2004/0093039 A1 | 5/2004 | Schumert | 607/40 |
| 2004/0133089 A1 | 7/2004 | Kilcoyne et al. | 600/350 |
| 2004/0147816 A1 | 7/2004 | Policker et al. | 600/300 |
| 2004/0162595 A1 | 8/2004 | Foley | 607/40 |
| 2004/0167583 A1 | 8/2004 | Knudson | 607/40 |
| 2004/0172084 A1 | 9/2004 | Knudson | 607/40 |
| 2004/0172085 A1 | 9/2004 | Knudson | 607/40 |
| 2004/0172086 A1 | 9/2004 | Knudson | 607/40 |
| 2004/0172088 A1 | 9/2004 | Knudson | 607/40 |
| 2004/0172095 A1 | 9/2004 | Jenkins | 607/116 |
| 2004/0176812 A1 | 9/2004 | Knudson | 607/40 |
| 2004/0236381 A1 | 11/2004 | Dinsmoor | 607/40 |
| 2004/0236382 A1 | 11/2004 | Dinsmoor | 607/40 |
| 2005/0021101 A1 | 1/2005 | Chen et al. | 607/40 |
| 2005/0038454 A1 | 2/2005 | Loshakove | 606/153 |
| 2005/0049655 A1 | 3/2005 | Boveja | 607/58 |
| 2005/0055039 A1 | 3/2005 | Burnett et al. | |
| 2005/0065575 A1 | 3/2005 | Dobak | |
| 2005/0090873 A1 | 4/2005 | Imran | |
| 2005/0096514 A1 | 5/2005 | Starkebaum | |
| 2005/0113880 A1 | 5/2005 | Gordon et al. | 436/106 |
| 2005/0131485 A1 | 6/2005 | Knudson | 607/40 |
| 2005/0131486 A1 | 6/2005 | Boveja | |
| 2005/0131487 A1 | 6/2005 | Boveja | |
| 2005/0137643 A1 | 6/2005 | Mintchev | |
| 2005/0137644 A1 | 6/2005 | Boveja | |
| 2005/0149141 A1 | 7/2005 | Starkebaum | 607/40 |
| 2005/0149142 A1 | 7/2005 | Starkebaum | 607/40 |
| 2005/0149146 A1 | 7/2005 | Boveja | |
| 2005/0159800 A1 | 7/2005 | Marshall | 607/122 |
| 2005/0159801 A1 | 7/2005 | Marshall | 607/122 |
| 2005/0216064 A1 | 9/2005 | Heruth et al. | |
| 2005/0222637 A1 | 10/2005 | Chen | |
| 2005/0222638 A1 | 10/2005 | Foley | 607/40 |
| 2005/0251219 A1 | 11/2005 | Evans | |
| 2006/0020298 A1 | 1/2006 | Camilleri et al. | |
| 2006/0025654 A1 | 2/2006 | Suzuki | |
| 2006/0036293 A1 | 2/2006 | Whitehurst et al. | |
| 2006/0058851 A1 | 3/2006 | Cigaina | |
| 2006/0074335 A1 | 4/2006 | Ben-Oren | |
| 2006/0074450 A1 | 4/2006 | Boveja et al. | |
| 2006/0074457 A1 | 4/2006 | Imran et al. | |
| 2006/0074458 A1 | 4/2006 | Imran | |
| 2006/0085054 A1 | 4/2006 | Zikorus et al. | |
| 2006/0089571 A1 | 4/2006 | Gertner | |
| 2006/0089690 A1 | 4/2006 | Gerber | |
| 2006/0095078 A1 | 5/2006 | Tronnes | |
| 2006/0116736 A1 | 6/2006 | DiLorenzo | |
| 2007/0049986 A1 | 3/2007 | Imran | |

| | | | | |
|---|---|---|---|---|
| 2008/0051850 | A1 | 2/2008 | Sparks et al. | |

FOREIGN PATENT DOCUMENTS

| | | | | |
|---|---|---|---|---|
| EP | 0129483 | 12/1984 | .................. | 1/36 |
| EP | 0 571 938 | 12/1993 | | |
| EP | 0571938 | 12/2001 | .................. | 1/36 |
| WO | WO 9843700 | 10/1998 | | |
| WO | 9853878 | 12/1998 | .................. | 1/5 |
| WO | WO 98/53878 | 12/1998 | | |
| WO | WO 0030534 | 6/2000 | | |
| WO | 0158389 | 8/2001 | .................. | 2/48 |
| WO | WO 01/58389 | 8/2001 | | |
| WO | 0176690 | 10/2001 | .................. | 1/18 |
| WO | WO 01/76690 | 10/2001 | | |
| WO | WO 0176690 | 10/2001 | | |
| WO | WO 0226101 | 4/2002 | | |

OTHER PUBLICATIONS

Keith E. Kelly, et al., Pacing The Canine Stomach With Electric Stimulation, *Am. J. of Physiology*, 222/3:588-594 (Mar. 1972).

J. Chris Eagon et al., Gastrointestinal Pacing, *Surgical Clinics of North America*, 73/6:1161-1172 (Dec. 1993).

H. Geldof, et al., Electrogastrographic Study of Gastric Myoelectrical Activity In Patients With Unexplained Nausea And Vomiting, *Gut*, 27:799-808, (1986).

Brent W. Miedema, et al., Pacing The Human Stomach, *Surgery*, 143-150, (Feb. 1992).

Keith A. Kelly, Differential Responses Of The Canine Gastric Corpus And Antrum To Electric Stimulation, *Am. J. of Physiology*, 226/1:230-234, (Jan. 1974).

Electric Stimulation of the Gastrointestinal Tract, GP, p. 151 (Apr. 1964).

Michael P. Hocking, Postoperative Gastroparesis And Tachygastria—Response to Electric Stimulation and Erythromycin, *Surgery*, 114/3:538-542 (Sep. 1993).

Keith A. Kelly et al., Role of the Gastric Pacesetter Potential Defined by Electrical Pacing, *Canadian J. of Physiology and Pharmacology*, 50:1017-1019, (1972).

Babajide O. Familoni, Efficacy of Electrical Stimulation at Frequencies Higher Than Basal Rate in Canine Stomach, *Digestive Diseases and Sciences*, 42/5:892-897, (May 1997).

Bader-Eddine Bellahsene, et al., Evaluation of a Portable Gastric Stimulator, Ninth Annual Conference of the Engineering in Medicine and Biology Society, (1987).

J. Chris Eagon, et al., Effects of Gastric Pacing on Canine Gastric Motility and Emptying, *The American Physiological Society*, 265/4:G767-G774, (Oct. 1993).

S. K. Sarna, et al., Electrical Stimulation of Gastric Electrical Control Activity, *Am. J. of Physiology*, 225/1:125-131, (Jul. 1973).

S. K. Sarna, et al., Gastric Pacemakers, *Gastroenterology*, 70:226-231, (1976).

Edwin E. Daniel, et al., Electrical Activity of the Gastrointestinal Tract as an Indication of Mechanical Activity, *Am. J. of Digestive Diseases*, 8/1:54-102, (1963).

Cigaina et al., "Gastric Myo-Electrical Pacing As Therapy For Morbid Obesity: Preliminary Results," Obes Surg;9:333-334, (1999).

Familoni, et al., "Electrical Pacing of the Stomach in Dogs, Engineering in Medicine and Biology Society," IEEE Proceedings of the Annual International Conference, 6:2315-2316 (Oct. 29-Nov. 1, 1992).

Office Action of U.S. Appl. No. 11/249,661, dated Dec. 12, 2007, 9 pages total.

Final Office Action of U.S. Appl. No. 11/249,661, dated Sep. 16, 2008, 9 pages total.

Office Action of U.S. Appl. No. 11/249,661, dated May 14, 2009, 8 pages total.

M. Kubota, ert al., Manometric Evaluation Of Children With Chronic Constipation Using a Suction-Stimulating Electrode, *Eu. J. Pediari. Surg.*, 2:287-290, (1992).

\* cited by examiner

ABDOMINALLY IMPLANTED STIMULATOR AND METHOD

RELATED APPLICATION DATA

This application is a continuation-in-part of U.S. patent application Ser. No. 10/295,128; which is a divisional of U.S. application Ser. No. 09/847,884, filed on May 1, 2001 (now U.S. Pat. No. 6,535,764); the full disclosure of which are incorporated herein by reference.

FIELD OF THE INVENTION

This invention relates to an anchor for attaching to the wall of a contractile organ such as, e.g., a stomach or other gastrointestinal tract organ.

BACKGROUND OF THE INVENTION

Digestive organ and other contractile organ stimulation using electrodes coupled to the organ have been proposed in a variety of applications. Currently devices for stimulating digestive tract organs are typically delivered to the organ by way of a laparoscopic surgical procedure, i.e., in which an incision is made in the stomach and the leads are tunneled through the abdominal tissue.

Copending parent application Ser. No. 10/295,128 filed Nov. 14, 2002 and its parent application Ser. No. 09/847,884 now U.S. Pat. No. 6,535,764 both of which are incorporated in their entirety herein by reference, describe an endoscopically delivered stimulation device that is attached to the inside of the stomach from within the stomach.

It would be desirable to provide an improved device system or method for attaching a device to a contractile organ such a stomach. It would also be desirable to provide an improved lead for stimulating a contractile digestive organ.

SUMMARY OF THE INVENTION

According to the present invention, a retention device, system and method are provided for attaching or coupling to a contractile organ. The device may be used to attach devices or elements such as, therapeutic or diagnostic devices or elements. According to one aspect of the invention a lead with such a retention device, is provided with at least one electrode for stimulating the organ. The retention device, system and method may also be used to couple devices or elements to a digestive tract organ such as a stomach. Such elements may include, but are not limited to, sensors for sensing conditions relating to the organ and therapeutic delivery systems such as drug delivery systems.

One aspect of the present invention provides a device, system and method for diagnosing and treating digestive related disorders or conditions. The present invention also provides a device, system and method for electrical stimulation of the digestive tract and related organs. Electrical stimulation is generally defined herein to mean any application of an electrical signal or of an electromagnetic field to tissue of the digestive organ for a therapeutic purpose. While the device system and method may be used with any digestive tract organ and/or gastrointestinal tract organ, it is described with particular reference to use in a stomach.

In one variation, stimulation is applied to the stomach, for example, to treat digestive disorders or conditions, nausea, obesity or pain symptoms. The stimulation may affect the smooth muscle contractions and/or nerves associated with the stomach. Stimulation may also be used to affect motility. In one variation, the device is designed to facilitate or expedite mixing or breaking down of food matter or liquids in the stomach. In another variation, the device is designed to control, facilitate or expedite movement of food matter or liquids through the stomach and into the small intestine. In another variation, the device is designed to stimulate the stomach to delay passage of food from the stomach and into the small intestine.

The device of an embodiment of the present invention may reside in part or in whole within the patient's stomach. A device may include: a lead including at least one stimulating electrode in electrical contact with the stomach wall when implanted. It may also include an electronics unit containing the electronic circuitry of the device; or an attachment or coupling system for attaching or coupling a device or lead to the stomach.

The device of the present invention may be deployed from an abdominal approach (e.g., using open or laparoscopic surgery) or an endoscopic approach (through the esophagus), or a combination of approaches.

In one embodiment the device comprises an anchor that engages the wall on one side of an organ. The anchor may be a disc, a plate, a stop, or other attachment device. The device further comprises an elongate portion extending through the organ wall wherein the elongate portion comprises a tapered portion tapering from an distal location with respect to the anchor towards a proximal location with respect to the anchor.

According to one variation, the anchor is positioned on the outside of the stomach wall when deployed. When deployed, the tapered portion of the elongate portion is configured to extend at least in part into the stomach wall from within the stomach and to permit the stomach wall to thicken as it contracts while generally maintaining the anchor in an engaging relationship with the outside of the stomach wall. During stomach contractile behavior, the stomach muscle contracts about the circumference of the tapered portion of the anchor which acts to hold the anchor in place. The contraction force vector on the tapered portion tends to pull the anchor in towards the outer wall of the stomach. As the stomach wall thickens it expands towards the wider portion of the taper and the anchor is held in place with gradually greater force as the stomach expands and the axial component of the contraction force increases.

A lead in accordance with the invention comprises the anchor and tapered member as described herein with an electrode or electrodes located thereon where the anchor and tapered member assist in maintaining electrical contact of the electrode(s) with the stomach wall. In pulling the engaging portion of the anchor towards the outer wall of the stomach as the stomach contracts, the anchor and tapered member accordingly act to reduce movement of the lead with respect to the stomach wall and thus to maintain electrode contact with the stomach wall.

According to one embodiment a device and method for laparoscopically implanting the device is provided. Such laparoscopically implantable device may include a subcutaneously implanted pulse generator coupled to a lead implanted through the stomach wall.

According to one embodiment, the stimulation device is constructed of size and shape such that it can be deployed through the mouth and esophagus with the aid of an endoscope. The device components may also be constructed of materials that allow it to withstand and function in the highly acidic environment of the stomach for two or more years.

In addition to the device being capable of stimulating the stomach wall, the device may also include diagnostic elements such as e.g., sensors for sensing various parameters of the stomach. The sensors may be mounted on the electronics unit, an attachment mechanism, the lead, or otherwise, for example, in an independently attached device. The stimulation device may include a mechanical sensor that senses, for example, stomach wall contractions. Alternatively, electrical sensors may detect changes in impedance due to changes in wall thickness from smooth muscle contractions. Other examples of such sensors may include, for example, pH sensors, impedance sensors, pressure sensors and temperature measuring devices The stimulation device may be programmed to deliver stimulation in response to sensing stomach parameters. For example, a sensor may be used to determine when food has been ingested. When the sensor senses information indicating food has been ingested, the stimulation device may be instructed to deliver stimulation pulses to stimulate gastric motility, to slow the emptying of the stomach, or to provide a sensation of fullness or satiety. The device may also be user controlled, where the recipient of the device is able to externally activate the device, for example by using an external unit which delivers a control signal via telemetry. Pressure sensors may be used to sense motility patterns, e.g. presence, strength or frequency of contractions. Mean pressure shifts may be observed to identify fundal contractility. The stimulation device may also use sensed parameters to program or reprogram the device stimulation program. For example, measuring impedance changes through a circuit coupled to the electrodes (e.g., delivering a constant current or voltage across the electrodes to determine impedance) or determining the contractile behavior of the stomach using a strain gauge (or similar sensor such as a piezo-electric sensor) in response to stimulation pulses, the effectiveness of the stimulation pulses may be monitored and adjusted to provide optimal response. Examples of use of such sensors are described, for example in copending U.S. application Ser. No. 10/950,345 filed Sep. 23, 2004, which is incorporated in its entirety herein by reference.

According to another aspect of the invention the device may be programmed to randomly or pseudorandomly select or vary one or more stimulation parameters, for example, to reduce adaptation or desensitization of a digestive organ to stimulation, and especially stimulation at non-physiologic rates.

Various aspects of the invention are further described in the following detailed description and in the claims herein.

DETAILED DESCRIPTION OF THE DRAWINGS

DETAILED DESCRIPTION OF THE PREFERRED EMBODIMENTS

Figure 1A:
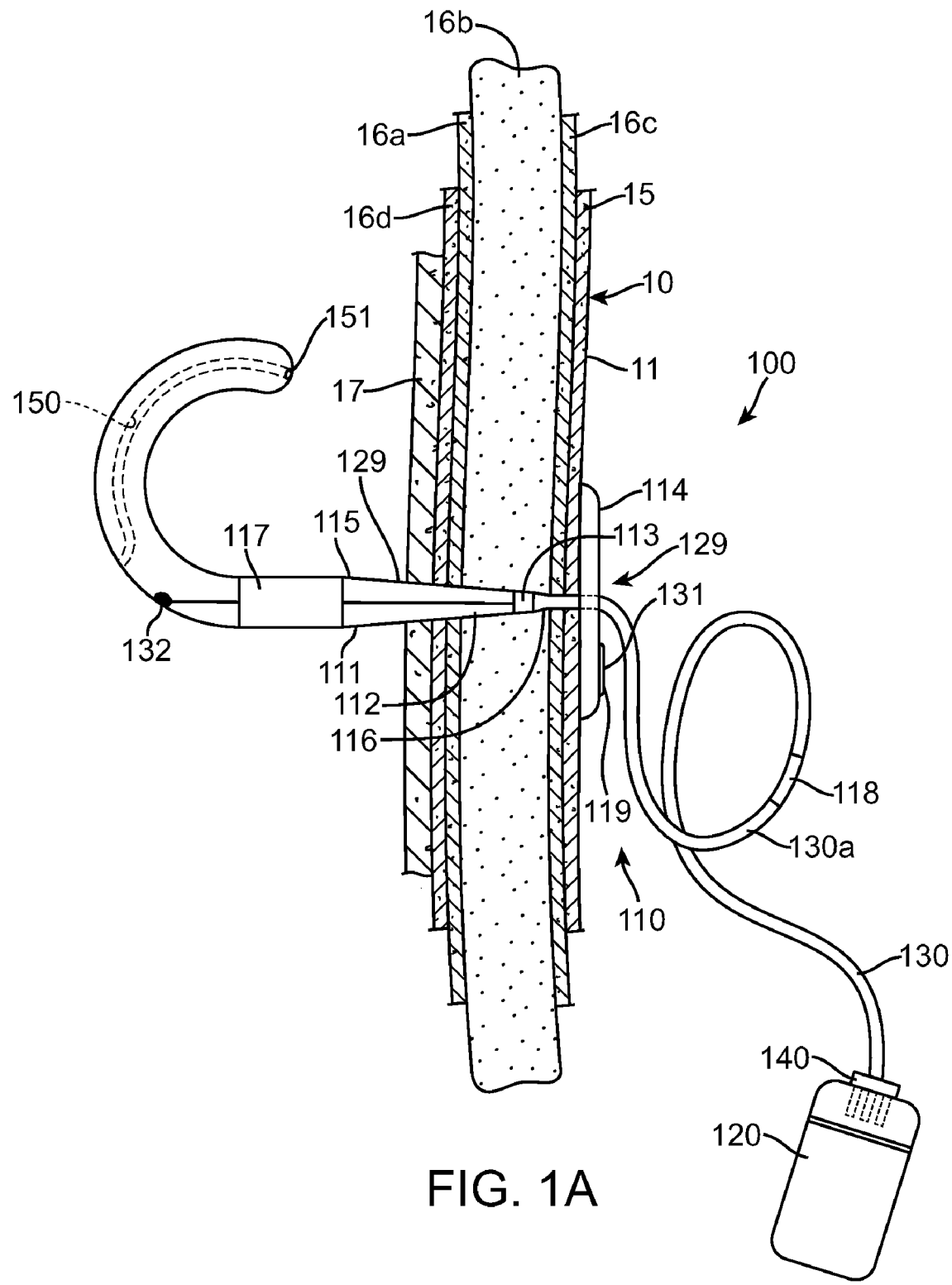
FIG. 1A is a schematic, partial cross section side view of a stimulator in accordance with the invention, implanted in a stomach.

Referring to FIG. 1A, a laparoscopically implantable stimulator 100 is illustrated implanted in a subject. The stimulator 100 includes a lead 110 (shown implanted in a stomach wall 10) coupled to stimulation electronic circuitry 120, (in this particular illustration, a subcutaneously implanted pulse generator). The lead 110 comprises a retaining portion 119 including an elongate portion 111 coupled to an expandable anchor 114 where the expandable anchor 114 engages the outside 11 of the stomach wall 10 and the elongate portion 111 extends through the stomach wall 10 and into the stomach. The lead 110 further comprises a lead wire 130 extending from the expandable anchor 114 to a connector 140 for connecting to the electronic circuitry 120 of the pulse generator.

The elongate portion 111 of the lead 110 includes a tapered portion 112 that tapers from an inward location 115 where the circumference of the tapered portion 112 is wider in a direction towards the outside of the stomach, to an outward location 116 where the circumference of the tapered portion 112 is narrower. When the lead 110 is deployed, the tapered portion 112 extends at least in part into the stomach wall. An electrode 113 is located on the elongate anchor 114 so that when the lead is implanted, the electrode 113 is located between the serosa 15 and mucosa 17 in one or more of the muscle layers 16a-c or submucosa 16d. A return electrode 117 is located on the elongate portion 111 within the stomach 10 (alternatively within the stomach wall 10). Return electrodes may be positioned in other locations. For example, a return electrode 118 may be located on the lead wire 130. A return electrode 119 may also be located on expandable anchor 114 (e.g., the outer surface of the anchor 114).

The expandable anchor 114 forms a plate that engages the outside 11 of the stomach wall 10 to prevent the lead from advancing further into the stomach and to maintain the relative position of the electrode 113 within the stomach wall. The expandable anchor 114 may alternatively or in addition include anchoring features such as, e.g., holes to receive sutures. The lead wire 130 includes some slack 130a to allow for movement of the patient, e.g. movement of the stomach during contractions or otherwise.

The tapered portion 112 of the elongate portion 111 operates to hold the electrode in place in the muscle layer during the stomach wall contraction. The contraction forces of the muscle layer translate into forces that hold the lead in the stomach. At the same time the forces of contraction draw the tapered lead in towards the inside of the stomach, the plate or expandable anchor 114 prevents movement of the lead further into the stomach.

Thus, the tapered portion 112 of the elongate member 111 acts to reduce movement of the lead 110 with respect to the stomach wall 10. The tapered configuration of the elongate portion 111 further permits the stomach wall to thicken while the lead 110 is held in place with gradually greater force. The tapered portion 112 and expandable anchor 114 accordingly assist in maintaining electrical contact of the electrode with the stomach wall by reducing movement of the anchor with respect to the stomach wall.

The lead 110 or a portion of the lead 110 (including, e.g. the tapered portion 112) may be constructed of a flexible or rigid material. According to one variation, a soft elastic material is used. When the stomach contracts the soft elastic material, the shape may change. Examples of such materials include, a fluoropolymer such as PTFE (polytetrafluoroethylene) or PVTF (polyvinitidine fluoride).

The lead 110 also includes a guidewire opening 150 and through hole 151 for guiding the lead 110 during deployment.

Figure 1B:
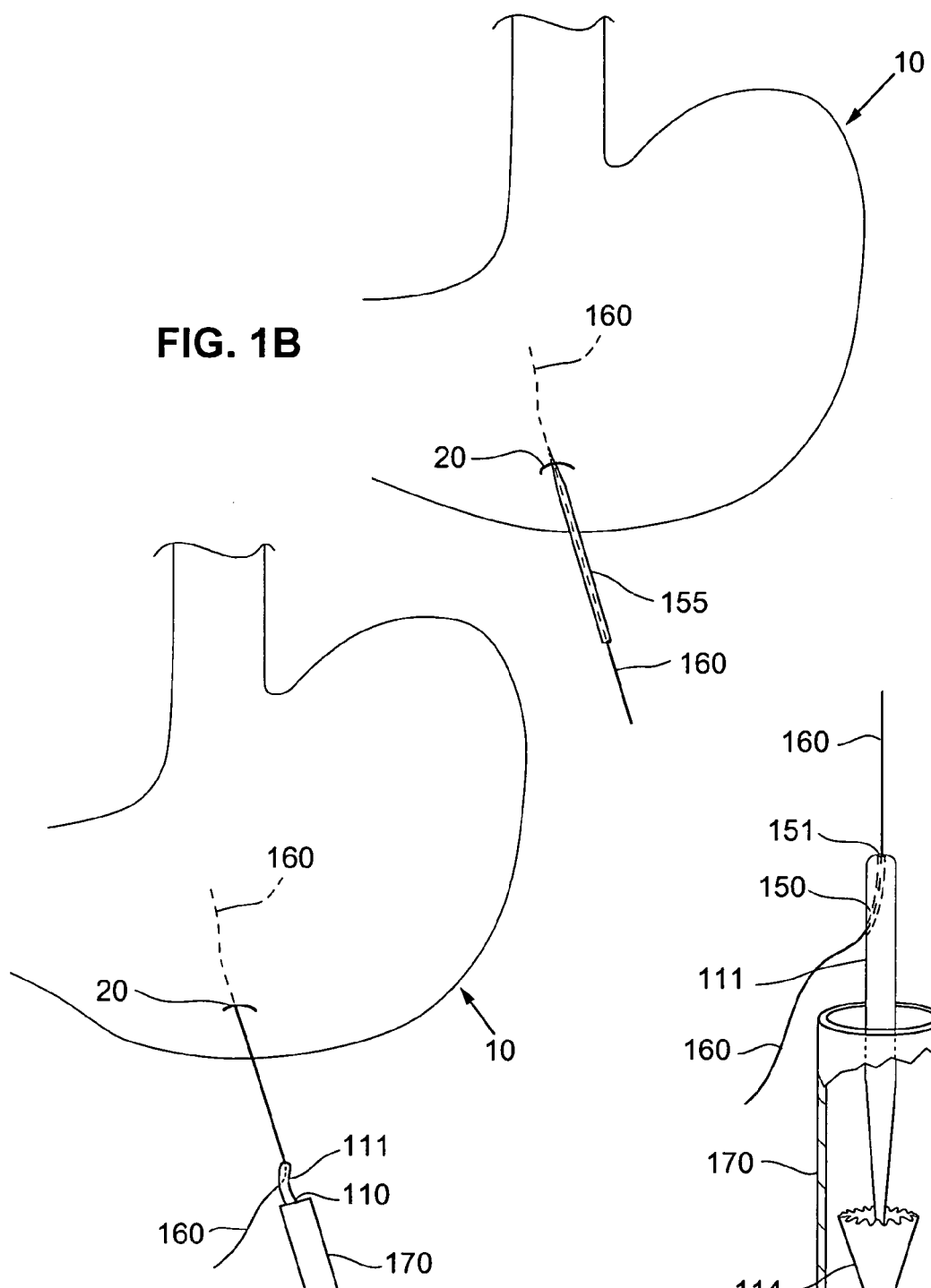
FIGS. 1B-1D illustrate a method for deploying the lead of FIG. 1A.
Figure 1C:
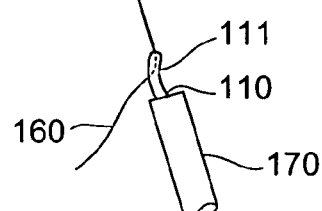
Figure 1D:
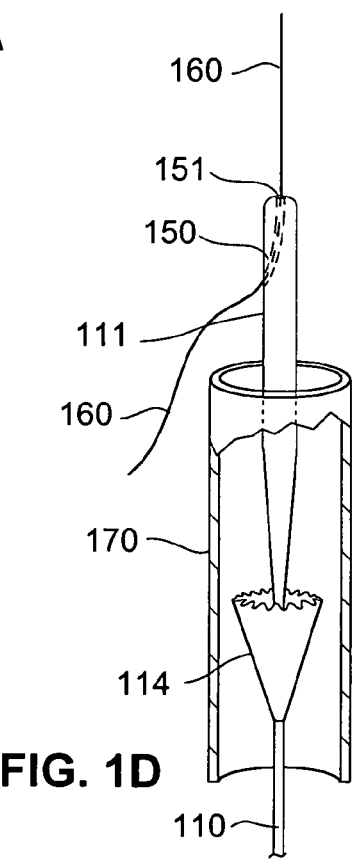

FIGS. 1B-1D illustrate deployment of the lead 110 using a laparoscopic system and method. As illustrated in FIG. 1B, the stomach 10 is punctured with a hollow needle 155 from the outside of the stomach into the stomach. A guidewire 160 is positioned through the needle 155 and into the stomach.

As illustrated in FIG. 1C, the needle 155 is removed leaving guidewire 160 in place extending through the abdomen into the stomach at a lead deployment site 20. A lead 110 with an expandable anchor 114 folded in a sheath 170 (FIG. 1D) is placed over the guide wire 160 through the guidewire lumen 150 and through hole 151 in the elongate portion 111 of the lead 110. The lead 110 is pushed over the guidewire 160 into place through the stomach wall 10 with the expandable anchor 114 adjacent the outside 11 of the stomach 10 at the deployment site 20. The sheath 170 is torn off the expandable anchor 114 and remaining lead 110 to allow the expandable anchor 114 to expand adjacent the outside 11 of the stomach wall 10. The expandable anchor 114 may then be finally adjusted to be in a position flush against the outer wall 11. The expandable anchor 114 may be sutured to the outside of the stomach wall through suture holes (not shown) provided in the expandable member.

A plurality of such leads may be each separately placed according to this procedure and then may be connected to the pulse generator. Also a plurality of leads may be attached to a single lead wire connector and placed in series.

A sensor may be included at one or more locations on the lead 110 or housing of the electronic circuitry. A sensor 131 is positioned on the expandable anchor 114 and may include a motion sensor or contraction sensor that senses movement or contraction of the stomach. For example, a piezoelectric sensor or strain gauge may be used to sense contractions. A sensor 132 such as a temperature or other sensor is located on the lead 110 within the stomach to determine when food has been ingested and/or to identify the composition of materials within the stomach. Examples of the use of such sensors are described in copending U.S. application Ser. No. 10/950,345 filed Sep. 23, 2004 incorporated herein by reference.

A number of variations are contemplated herein. For example, the electronic circuitry may be attached to the stomach wall in a housing or may include an external device in communication with electronic circuitry implanted in the patient. The return electrode or second electrode of a bipolar pair of stimulation electrodes may be located on the expandable member, along the lead inside or outside of the stomach or within the stomach wall. The return electrode may also be included in a separately implanted lead similar to lead 110. The return electrode may also be located on the electronics housing. The expandable member may alternatively comprise an anchor or attachment device that attaches to any portion of the stomach wall. The device may also be implanted in other digestive organs or contractile organs with cavities.

Figure 2:
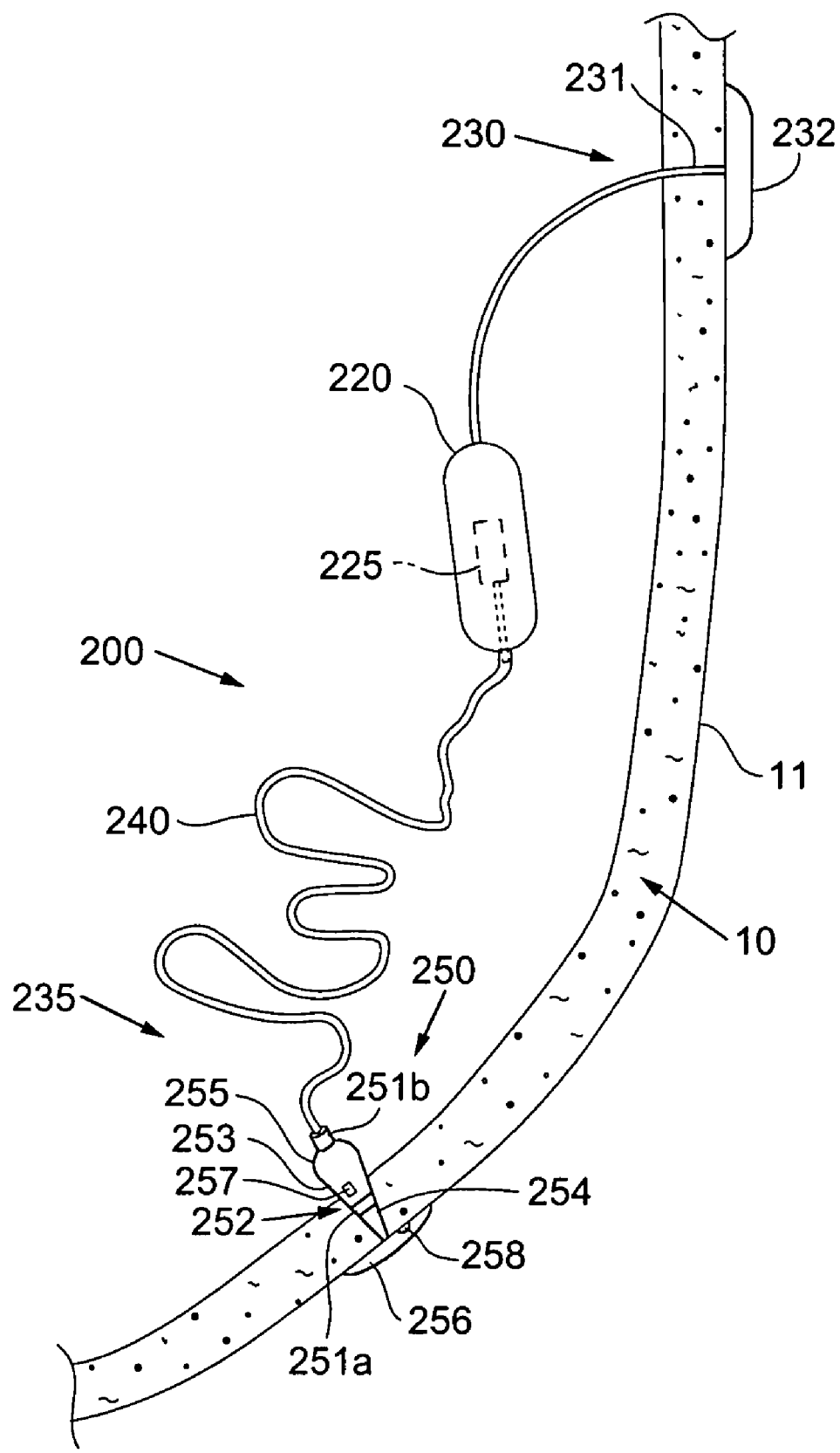
FIG. 2 is a schematic, partial cross section side view of a stimulator in accordance with the invention, implanted in a stomach.

Referring to FIG. 2, a stimulator 200 in accordance with the invention is illustrated attached to a stomach wall 10. The stimulator 200 comprises a housing 220 containing electronic circuitry 225 and attached with anchor 230 to the stomach wall 10. The anchor 230 comprises an elongate member 231 having an expandable distal portion 232. The expandable distal portion 232 may be deployed from the inside to the outside of the stomach wall where the expandable distal portion 232 is expanded to engage the outer surface 11 of the stomach wall 10. The elongate member 231 extends through the stomach wall between the expandable distal portion and the housing containing the electronic circuitry 225 to attach anchor 230 to the housing 220. An example of the deployment of an expandable member such as the expandable distal portion 232 is described, for example, in U.S. Pat. No. 6,535,764 incorporated herein by reference. The expandable distal portion may comprise, for example, a shape memory alloy, a spring member, or an inflatable member. The electronic circuitry is sealed in the housing 220. The electronic circuitry 225 provides an electrical signal applied through electrodes to the stomach wall, and telemetry communication with an external unit such as a programmer, reader, recorder or controller. The outer shell of the housing 220 is constructed of an acid corrosion resistant material such as a suitable inert polymer that is stable in acidic environments, or an acid corrosion resistant metal such as Platinum, Gold, Tantalum, Titanium, or suitable alloys thereof.

The stimulator 200 further comprises a lead 235 in accordance with the invention. The lead 235 is coupled to the electronic circuitry 225 of the housing 220 with a flexible lead wire 240. The lead 235 extends out of the housing 220 and is positioned through the stomach wall 10 with at least one electrode in contact with tissue of the stomach.

The lead 235 comprises a retaining portion 250 including an elongate portion 252 that when deployed, extends through the stomach wall 10. The elongate portion 252 comprises a tapered portion 253 that when deployed, extends at least in part, through the stomach wall 10. The retaining portion 250 further comprises an expandable distal anchor portion 256 that may be deployed from the inside the stomach to the outside of the stomach wall in a manner similar to the deployment of the expandable distal portion 232. The expandable distal anchor portion 256 is expanded at the outside surface 11 of the stomach and is configured to engage the outer surface 11 of the stomach wall 10. The expandable distal anchor portion 256 acts as a stop to prevent the retaining portion 250 from pulling out and into the stomach. The elongate portion 252 extends at least in part through the stomach wall 10 and between the expandable distal anchor portion 256 and the housing 220.

The tapered portion 253 of the elongate portion 252 comprises a narrower portion 254 located outwardly towards the outside of the stomach with respect to a wider portion 255 which is more inward. The tapered portion 253 tapers from the wider portion 255 outwardly towards the narrower portion 254. The retaining portion 250 further comprises a first electrode 251a and a second electrode 251b, each electrode formed of a corrosion resistant metal conductor such as Platinum, Gold, Tantalum, Titanium or suitable alloys thereof. The first electrode 251a comprises a small ring electrode positioned on the narrower portion 254 and in electrical contact with the stomach wall 10. The second electrode 251b is located proximally of the first electrode 251a near the wider portion 255 of the elongate member 253. The second electrode 251b has a significantly greater surface area than the first electrode 251 thus focusing the current density adjacent the first electrode 251a. The electrodes 251a, 251b are coupled to conductors extending through flexible lead wire 240, which are coupled to the electronic circuitry 225.

The tapered portion 253 of the elongate member 252 acts to reduce movement of the retaining portion 250 with respect to the stomach wall 10 in a manner similar to that described with reference to retaining portion 119 of FIG. 1A. A sensor 257 may also be located on or adjacent the elongate portion 252 or other portion of the retaining portion 250. A sensor 258 may be located on a portion of the anchor adjacent the stomach wall, such as e.g. on the expandable distal portion 256. For example, sensor 257 or sensor 258 may comprise a temperature sensor or contraction sensor (such as a piezo-electric element or strain gauge), or other sensor indication a condition relating to the stomach. Sensors 257, 258 may be coupled through a conductor extending through the lead wire 240 to the electronic circuitry 225 in the housing 220.

The lead 235 or a portion of the lead 235 (including, e.g. the tapered portion 253) may be constructed of a flexible or rigid material. According to one variation, a soft elastic material is used. When the stomach contracts the soft elastic material, the shape may change. Examples of such materials include, a fluoropolymer such as PTFE (polytetrafluoroethylene) or PVTF (polyvinitidine fluoride).

The circuitry 225 comprises, a microprocessor or controller for controlling the operations of the electronic circuitry 225, an internal clock, and device configured to power the various components of the circuit 225. The controller controls electrical stimulation delivered to stimulating electrodes 251a, 251b in accordance with programmed parameters.

Figure 3:
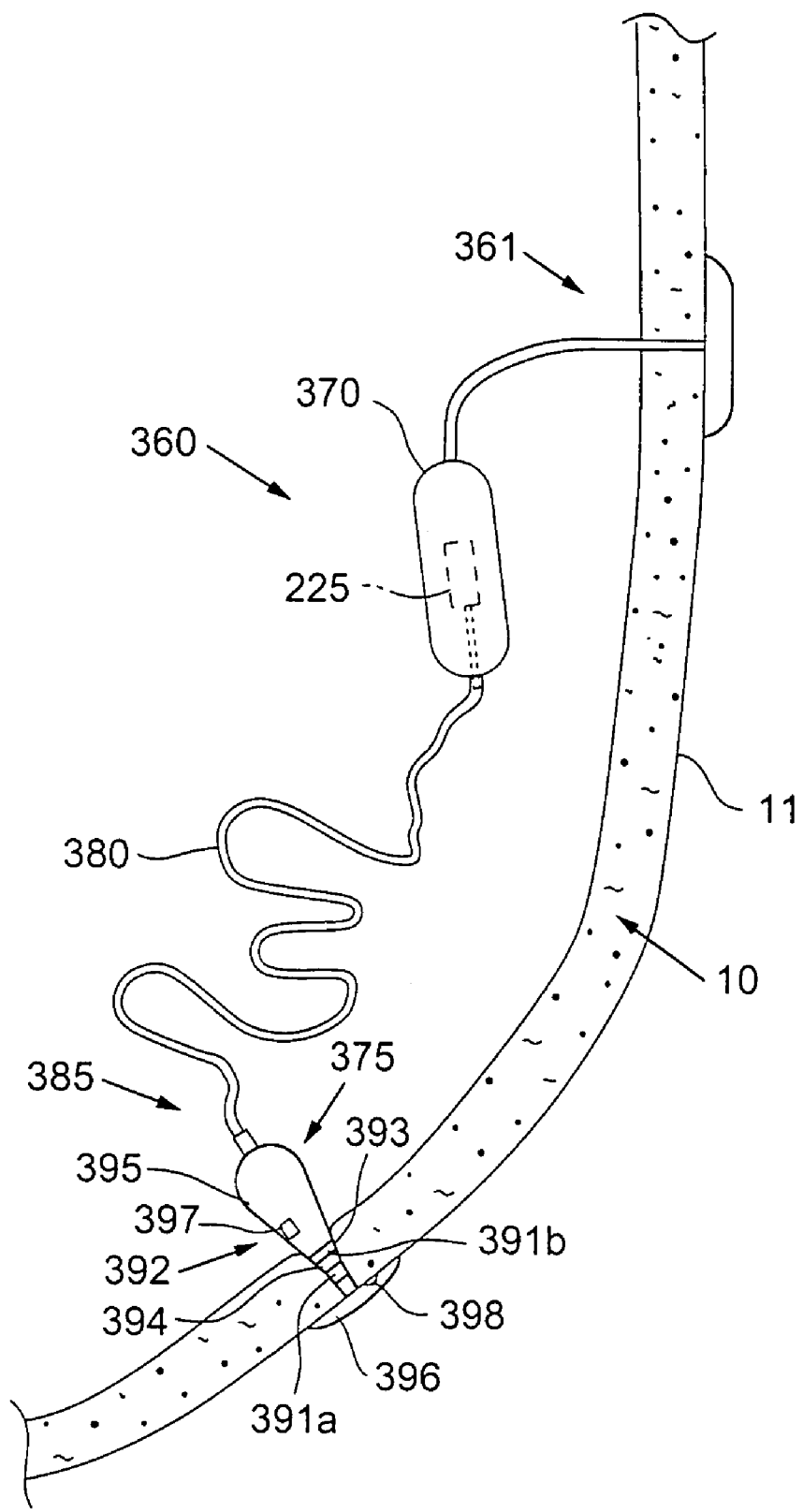
FIG. 3 is a schematic, partial cross section side view of a stimulator in accordance with the invention, implanted in a stomach.

FIG. 3 illustrates a stimulator 360 in accordance with the invention attached to a stomach wall 10. The stimulator 360 comprises a housing 370 containing electronic circuitry 225 described above with reference to FIG. 2. The housing 370 is constructed in a similar manner as housing 220 and is attached with anchor 361 to the stomach wall in a similar manner as the housing 220 is attached as described with respect to FIG. 2.

The stimulator 360 further comprises a lead 375 in accordance with the invention. The lead 375 is coupled to the electronic circuitry 225 of the housing 370 with a flexible lead wire 380. The lead 375 extends out of the housing 370 and is positioned through the stomach wall 10 with a bipolar electrode pair 391a, 391b in contact with tissue of the stomach.

The lead 375 comprises a retaining portion 385 including an elongate portion 392 that when deployed, extends through the stomach wall 10. The elongate portion 392 comprises a tapered portion 393 that when deployed and when the stomach is contracting, extends at least in part, through the stomach wall 10. The retaining portion 385 further comprises an expandable distal anchor 396 that may be deployed from the inside the stomach to the outside of the stomach wall in a manner similar to the deployment of the expandable distal anchor 256 as described with respect to FIG. 2. The expandable distal anchor 396 is expanded at the outside surface 11 of the stomach and is configured to engage the outer surface 11 of the stomach wall 10. The expandable distal anchor 396 acts as a stop to prevent the retaining portion 385 from pulling out and into the stomach. The elongate portion 392 extends at least in part through the stomach wall 10 and between the expandable distal anchor 396 and the housing 370. The tapered portion 393 of the elongate portion 392 comprises a narrower portion 394 located outwardly towards the outside of the stomach with respect to a wider portion 395 which is more inward. The tapered portion 393 tapers from the wider portion 395 outwardly towards the narrower portion 394. The retaining portion 385 further comprises a pair of bipolar electrodes, 391a, 391b, each electrode formed of a corrosion resistant metal conductor such as Platinum, Gold, Tantalum, Titanium or suitable alloys thereof. The electrode pair 391a, 391b is positioned on the narrower portion 394 and in electrical contact with the stomach wall 10. The electrodes 391a, 391b are coupled to conductors extending through flexible lead wire 380, which are coupled to the electronic circuitry 225. The lead 375 may be constructed of similar materials as lead 253 as described herein.

The tapered portion 393 of the elongate member 392 acts to reduce movement of the retaining portion 385 with respect to the stomach wall 10 in a manner similar to that of retaining portion 119 described herein with reference to FIG. 1.

A sensor 397 may also be located on or adjacent the elongate portion 392 or other portion of the anchor 390. A sensor 398 may be located on a portion of the anchor adjacent the stomach wall, such as e.g. on the expandable distal portion 396. For example, sensor 397 or sensor 398 may comprise a temperature sensor or contraction sensor (such as a piezoelectric element or strain gauge), or other sensor indication a condition relating to the stomach. Sensors 397, 398 may be coupled through a conductor extending through the lead wire 380 to the electronic circuitry 225 in the housing 370.

Memory devices located in the electronic circuitry or implantable pulse generator(or alternatively in an external device in communication with the electronic circuitry) contain the program instructions for the controller and any other permanently stored information that allows the controller to operate. The memory device may also contain programmable memory. A telemetry coil or other communication device that communicates with an external control or programming device may also be provided. Thus information may be downloaded or uploaded from or to an external device. The electronic circuit 225 or pulse generator may also be coupled to one or more sensors.

The stimulation modes and parameters can either be set using the external programmer, or they may be set in response to sensory feedback.

According to one aspect of the invention, a device is provided that is programmed to randomly (or pseudorandomly) select or vary one or more stimulation parameters, and to deliver the stimulation to a digestive organ according to the selected parameters. In accordance with one aspect, stimulation is randomly (or pseudorandomly) selected or varied to reduce adaptation or desensitization of a digestive organ to stimulation, and especially to stimulation at non-physiologic rates. The programmed device may randomly (or pseudorandomly) select or generate parameters from within a window of acceptable parameters or a randomization window. Such parameters may include but are not limited to, e.g., pulse width, pulse repetition rate, burst frequency, burst repetition rate, pulses per burst. The programmed device may also randomly (or pseudorandomly) select or vary pulse amplitude, pulse shape and burst envelope within a window or according to selection criteria. The programmed device may randomly (or pseudorandomly) select or vary any one or more of these or other parameters prior to or during stimulation. The programmed device may also randomly (or pseudorandomly) select or vary stimulation from pulse to pulse or burst to burst. The programmed device may operate to periodically change parameters or may do so in response to sensing or receiving feedback that adaptation or desensitization is occurring, or that the stimulation is otherwise losing its effectiveness. According to one aspect of the invention, for example, the device may monitor stimulation response over time using a contraction monitoring device such as a strain gauge or other contraction sensor. If the device detects a sub optimal stimulation response, the device may then randomly or pseudorandomly select the next parameter(s)or sets of parameters. An example of such stimulation is described in co-pending U.S. application "Randomized Stimulation of A Gastrointestinal Organ" U.S application Ser. No. 11/219,004, filed on Sep. 1, 2005.

The electronic circuitry 225 or pulse generator may communicate with an external device that may be capable of receiving, displaying, or analyzing data from the electronic circuitry and also may be capable of programming, controlling or other communications with the electronic circuitry 225 or pulse generator. The electronic circuitry 225 may also comprise a passive device that may be powered and controlled by an external device.

A lead as described herein is also set forth in copending application entitled DIGESTIVE ORGAN RETENTION DEVICE filed on even date herewith and incorporated in its entirety herein by reference.

While the invention has been described with reference to preferred embodiments and in particular to a gastric stimulator, the present invention contemplates that the attachment devices may be used to attach a number of functional devices to the wall of digestive organs.

While the invention has been described with reference to certain embodiments, it will be understood that variations and modifications may be made within the scope of the following claims. Such modifications may include substituting elements or components which perform substantially the same function in substantially the same way to achieve substantially the same result that the invention can be practiced with modification within the scope of the following claims.

What is claimed is:

1. A method for laparoscopically implanting a lead in a digestive organ comprising the steps of:
   inserting a guidewire to an attachment site on the digestive organ so that the guidewire extends through a wall of the digestive organ between an internal cavity of the organ and an outer surface of the organ;
   providing a lead comprising:
      an anchor;
      a guidewire lumen including a distal through hole; and
      an electrode;
   inserting the guidewire through the through hole and through the guidewire lumen of the lead, and advancing the lead over the guidewire so that the lead extends through the wall of the digestive organ; and
   attaching the lead to the organ with the anchor extending along the outer surface of the organ so that the lead is implanted extending through the organ with the electrode in electrical contact with the tissue of the organ between the outer surface of the digestive organ and the internal cavity of the digestive organ.

2. The method of claim 1 wherein the step of providing a lead comprises:
   providing an expandable member in a first more narrow configuration enclosed by a sheath;
   wherein the step of inserting the lead over the guidewire comprises guiding the sheath with the guidewire to an anchor attachment site on the organ; and
   releasing the expandable member from the sheath to expand to a second wider configuration.

3. The method of claim 1 wherein the step of providing a lead comprises providing a lead with an elongate portion; and
   wherein the step of attaching the lead to the organ comprises inserting the elongate portion over the guidewire through the wall of the organ into the organ.

4. The method of claim 1, wherein the elongate portion is positioned so that a temperature sensor of the lead is disposed within the internal cavity of the digestive organ and separated from the wall of the digestive organ.

5. A method for implanting a lead in a digestive organ comprising the steps of:
   positioning a guidewire across a wall of the digestive organ;
   advancing a lead over the guidewire toward the digestive organ, wherein the lead includes an elongate portion, a sensor, an electrode, and an anchor;
   positioning the elongate portion across the wall of the digestive organ so that the anchor resides against an outer surface of the digestive organ, so that the sensor resides within an interior of the digestive organ, and so that the electrode is in electrical contact within the wall of the digestive organ;
   attaching the anchor to the outer surface of the digestive organ;
   stimulating the wall of the digestive organ with the electrode; and
   sensing within the interior of the digestive organ with the sensor.

6. The method of claim 5, wherein attaching comprises suturing the anchor to the outer surface of the digestive organ.

7. The method of claim 5, wherein sensing comprises sensing temperature.

8. The method of claim 5, wherein sensing comprises determining when food has been ingested.

9. The method of claim 5, wherein sensing comprises identifying a composition of a material.

10. The method of claim 5, further comprising laparascopically advancing a needle across the wall of the digestive organ and wherein positioning the guidewire comprises inserting the guidewire through the needle.

11. The method of claim 10, wherein advancing the needle includes advancing the needle toward the digestive organ by laparoscopy.

12. The method of claim 5, wherein the elongate portion includes a guidewire lumen extending at least partially therethrough, and wherein advancing the lead over the guidewire comprises passing the guidewire through the guidewire lumen.

13. The method of claim 5, wherein the anchor comprises an expandable anchor collapsible in a sheath, further comprising removing the sheath to allow the expandable anchor to expand for residing against the outer surface of the digestive organ.

14. The method of claim 5, wherein the sensor comprises a temperature sensor, and wherein the temperature sensor is positioned within the interior of the digestive organ separated from the wall of the digestive organ.

* * * * *

UNITED STATES PATENT AND TRADEMARK OFFICE
CERTIFICATE OF CORRECTION

| | |
|---|---|
| PATENT NO. | : 7,643,887 B2 |
| APPLICATION NO. | : 11/249291 |
| DATED | : January 5, 2010 |
| INVENTOR(S) | : Mir A. Imran |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1057 days.

Signed and Sealed this

Sixteenth Day of November, 2010

David J. Kappos
*Director of the United States Patent and Trademark Office*